US 6,530,375 B1

(12) United States Patent
Cieslik, Jr.

(10) Patent No.: US 6,530,375 B1
(45) Date of Patent: Mar. 11, 2003

(54) APPLIANCE TO CORRECT TEMPROMANDIBULAR JOINT SYNDROME AND METHODS OF MAKING AND USE

(76) Inventor: Charles R. Cieslik, Jr., 8519 Ramoort Dr., Baltimore, MD (US) 21236

(*) Notice: Subject to any disclaimer, the term of this patent is extended or adjusted under 35 U.S.C. 154(b) by 0 days.

(21) Appl. No.: 09/532,771

(22) Filed: Mar. 22, 2000

(51) Int. Cl.[7] .................................................. A61F 5/56
(52) U.S. Cl. ........................................ 128/848; 128/859
(58) Field of Search .......................... 128/848, 859–862; 433/6; 602/902

(56) References Cited

U.S. PATENT DOCUMENTS

| | | | | |
|---|---|---|---|---|
| 2,694,397 A | * | 11/1954 | Herms | 128/861 |
| 3,496,936 A | * | 2/1970 | Gores | 128/861 |
| 3,518,988 A | * | 7/1970 | Gores | 128/861 |
| 4,920,984 A | * | 5/1990 | Furumichi | 128/861 |
| 5,339,832 A | * | 8/1994 | Kittelsen | 128/859 |
| 5,365,945 A | * | 11/1994 | Halstrom | 128/848 |
| 5,513,656 A | * | 5/1996 | Boyd | 433/6 |
| 5,513,984 A | * | 5/1996 | Ueno | 128/861 |

* cited by examiner

*Primary Examiner*—Michael A. Brown
(74) *Attorney, Agent, or Firm*—Nixon & Vanderhye

(57) ABSTRACT

An appliance of relatively soft thermoplastic material is applied to the teeth of the mandible or maxilla and has contact points or fulcrums bisecting both premolars bilaterally up to the vertical midpoints of each premolar. By forming raised contact points or fulcrums, a pivoting location spaced from the tempromandibular joint is provided. When the individual clenches the teeth, the mandible pivots about the contact points or fulcrums of the appliance, relieving the pressure and stress on the joint, thereby relieving the symptoms and adverse effects of TMJS.

10 Claims, 5 Drawing Sheets

APPLIANCE TO CORRECT TEMPROMANDIBULAR JOINT SYNDROME AND METHODS OF MAKING AND USE

TECHNICAL FIELD

The present invention relates to a dental appliance to be worn on the mandible or maxilla to correct tempromandibular joint syndrome and particularly relates to an appliance having contact points forming bilateral fulcrums for pivoting the mandible relative to the maxilla upon clenching the teeth to relieve the syndrome.

BACKGROUND

Many individuals are affected by tempromandibular joint syndrome (hereafter called TMJS or the syndrome). This syndrome is often manifested by headaches, aches along one side of an individual's face, a ringing in the ear, sinusitis, soreness, limited range of motion and the like. The syndrome is quite debilitating for the afflicted individuals and is often misdiagnosed by medical professionals. For example, the syndrome has been misdiagnosed as an ear infection and the treatment following that diagnosis has little or no effect in relieving the effects of the syndrome. Dentists and others will sometimes misdiagnose the syndrome as a misalignment of the teeth. The efforts to bring the teeth into alignment, for example, by grinding selected teeth or applying splints, likewise do not relieve the effects of TMJS.

It is believed that the cause of TMJS is stress-induced clenching of the teeth. Individuals, when stressed, tend to clench their teeth, either consciously or unconsciously, and thereby apply constant or periodic tension to the muscles which cause the above-mentioned symptoms. Particularly, the tension caused by the musculature compresses the tempromandibular joint (hereafter the TMJ or the joint). When pressure is applied to the condyle and hence against the fossa during clenching, the cartilage or meniscus between those components is compressed. The bursa containing the synovial fluid also swells which brings about symptoms such as clogging of the ear and sinusitis. As noted previously, these symptoms are oftentimes misdiagnosed as an ear infection and treated accordingly, without relieving the effects of TMJS.

Current treatment modalities for TMJS when properly diagnosed includes application of moist heat, physical therapy, electroshock therapy, steroid injections, crowns for the teeth, splints and even joint replacement. Those treatments, however, often do not relieve the effects of TMJS and, accordingly, there is a need for an appropriate treatment of TMJS.

DISCLOSURE OF THE INVENTION

In accordance with a preferred embodiment of the present invention, there is provided a dental appliance which relieves the adverse effects of TMJS by relieving the pressure on the tempromandibular joint. Particularly, the appliance provides bilateral fulcrums between the teeth of the mandible and maxilla to extend or distract the tempromandibular joint. As a result, the pressure on the joint complex is released. Thus, instead of compressing the fossa/meniscus/condyle when the teeth are clenched, the opposite effect is achieved, i.e., a release of the pressure on the joint. This also releases the musculature involved in clenching. With respect to the lafter, the masseter, temporalis, sternocleidomastoid and trapezius muscles are typically flexed when the teeth are clenched. However, in accordance with the present invention and with use of the appliance hereof, those muscle groups are not only rested but are extended rather 405772 than flexed. The appliance thus affords relief to the meniscus, enabling the meniscus to heal. It also reduces the pressure on the bursa, thereby relieving the effects applied to the auditory canal and the sinuses, reducing muscle strain, eliminating spasms and headaches, and affording an appliance which is reusable at any time the symptoms of stress-induced TMJS occur.

Particularly, the appliance is preferably applied to the mandible but may be applied to the maxilla, with similar beneficial results. The appliance has bilateral contacts which, when the appliance is applied to the mandible, project toward and contact the teeth of the maxilla. Those contacts serve as fulcrums which, when the teeth are clenched, tend to relieve the pressure on the joint. More particularly, when properly formed and applied, the appliance causes contact with the teeth of the maxilla only at the contact points of the appliance on the mandible. This normally leaves gaps between the appliance and the front and back teeth of the maxilla. When the teeth are clenched, the gap between the front teeth closes, relieving the pressure on the tempromandibular joint and extending, rather than flexing, the associated musculature. The contact points are thus located such that the pivot points for the mandible relative to the maxilla shift from the joint to substantially a midpoint along the mandible, i.e., generally bisecting the premolars, as noted more particularly below. It will be appreciated that when the teeth are clenched, the front teeth close toward engagement, causing the pressure between the condyle and fossa to be relieved without causing a swelling of the cartilage or bursa sac. The contact points, i.e., the fulcrums, also alleviate the need to activate the muscle groups normally activated in response to clenching of the teeth. The appliance is preferably worn periodically, for example, at night, during sleep, and should be removed during the day.

Moreover, the appliance may be readily formed and fit for each individual afflicted with TMJS using conventional dental practice techniques. For example, discrete impressions of the teeth of the mandible and maxilla are made and positives are made from those impressions. The location of the bilateral fulcrums is significant as the fulcrums must be located to relieve the pressure on the joint during clenching. If the fulcrum is back too far, the back teeth will contact one another. If too far forward, there is insufficient clearance for displacement of the front teeth to effect a decompression of the joint. In accordance with the present invention, it has been found that the fulcrums should be located substantially adjacent the premolars, preferably bisecting both premolars bilaterally, without any other contact points between the appliance and teeth anteriorly or posteriorly of the two fulcrums. Thus, once the positives are formed, one of the positives, for example, the maxilla, can be notched at the fulcrums, i.e., at a location approximately over the second premolar and a portion of the first premolar. The mandible is then placed in a vacuum former and thermoplastic material is drawn about the mandible to form the appliance. While the plastic material is soft, the positive of the maxilla is brought to bear against the material whereby the material flows into the notches forming the fulcrums. Preferably, these contact points are flat along their projecting surfaces, both front-to-back and side-to-side. With the fulcrums thus formed, the appliance is removed from the vacuum former and applied to the patient. The appliance is then finely adjusted, e.g., by removing thermoplastic material at one or both of the fulcrums, to ensure that the fulcrums engage simultaneously in the patient's mouth without any other teeth abutting one another or abutting the appliance.

In a further preferred embodiment, the appliance may be fabricated from a positive of either the teeth of the mandible or maxilla. For example, where a positive model of the teeth of the mandible is formed by taking an impression, a pair of small plastic inserts or pieces may be located on top of the teeth at the predetermined location of the fulcrums. Thus, the plastic inserts can be adhered over the top of the teeth of the positive at the locations of the second premolar and a portion of the first premolar on opposite sides of the positive. With the inserts adhered to the positive of the mandibular model, the unit may be placed in a vacuum former and dental thermoplastic material is drawn about the mandible to form the appliance. It will be appreciated that the finished appliance when removed from the vacuum former will have a pair of projections or fulcrums at the desired locations. The thickness of each insert may be about 0.150 inches, while the thickness of the appliance material may likewise be about 0.150 inches, thus forming a fulcrum projecting from the appliance surface approximately 0.150 inches.

It will be appreciated that the appliance preferably extends in a full U-shaped arch. However, it can also be formed of two discrete bilateral sections rather than into a full arch. Further, rotation of the mandible about the fulcrum must be free, i.e., the front teeth must be spaced from one another prior to rotation. This ensures, that when the patient clenches, the contacts points cause the mandible to pivot forwardly and upwardly about the fulcrums, thereby relieving the pressure on the joint and alleviating the effects of TMJS.

In a preferred embodiment according to the present invention, there is provided an appliance for correcting tempromandibular joint syndrome comprising an appliance body for disposition along teeth on one of the mandible and the maxilla and having a contact projecting toward and for contacting the teeth of another of the mandible and the maxilla, whereby the contact serves as a fulcrum to relieve pressure on the tempromandibular joint in response to clenching of the teeth.

In a further preferred embodiment according to the present invention, there is provided an appliance for correcting tempromandibular joint syndrome comprising an appliance body for disposition along teeth on one of the mandible and the maxilla and having bilateral contacts projecting toward and for contacting the teeth of another of the mandible and the maxilla, whereby the contacts serve as fulcrums to relieve pressure on the tempromandibular joint in response to clenching of the teeth.

In a still further preferred embodiment according to the present invention, there is provided a method of treating tempromandibular joint syndrome comprising the steps of relieving the pressure on the tempromandibular joint by causing the mandible to pivot in a direction tending to displace the condyle away from the fossa.

In a still further preferred embodiment according to the present invention, there is provided a method of forming an appliance for correcting tempromandibular joint syndrome comprising the steps of forming an impression of the teeth of an individual's mandible and maxilla, forming a positive of the teeth of the mandible and maxilla from the impressions, providing bilateral notches in the teeth of one of the positives of the teeth of the mandible and maxilla, forming a soft plastic material about the teeth of another of the positives of the mandible and maxilla to form an appliance body and while the thermoplastic material is soft and formable, relatively closing the positives of the teeth of the mandible and maxilla toward one another such that the plastic material enters the notches, thereby forming an appliance having raised bilateral contact points for projecting toward opposed registering teeth in use.

In a still further preferred embodiment according to the present invention, there is provided a method of forming an appliance for correcting tempromandibular joint syndrome comprising the steps of forming an impression of the teeth of an individual's mandible or maxilla, forming a positive of the teeth of the mandible or maxilla from the impression, providing inserts at predetermined bilateral locations along the positive of the teeth of the mandible or maxilla and forming a soft plastic material about the inserts and the positive of the teeth of the mandible or maxilla to form an appliance body having raised bilateral contact points for projecting toward opposed registering teeth when the appliance is worn by an individual.

BEST MODE FOR CARRYING OUT THE INVENTION

Figure 1:
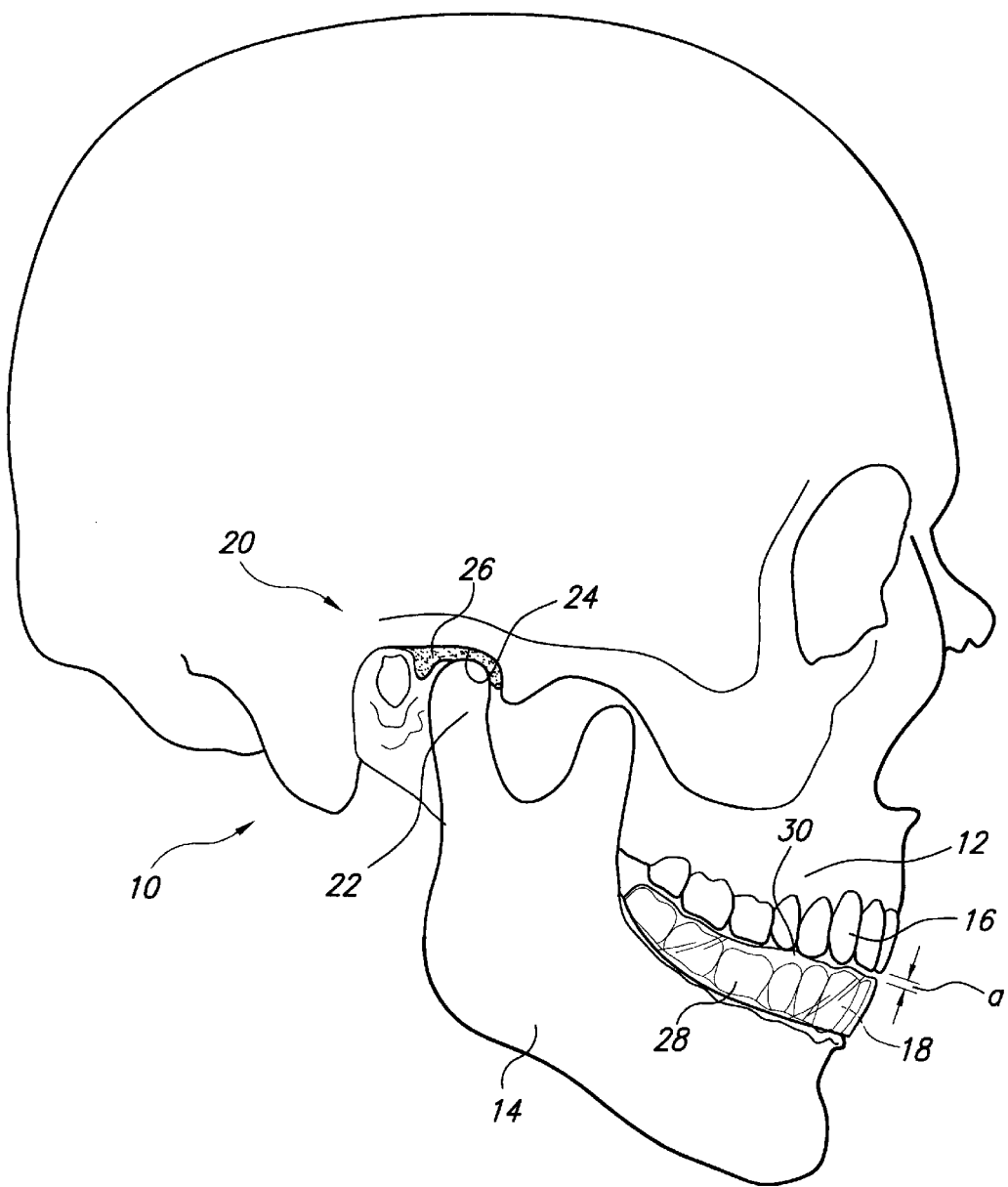
FIG. 1 is a schematic representation of an individual's head illustrating the tempromandibular joint, and the individual's teeth with an appliance constructed in accordance with the present invention disposed on the teeth of the mandible.

Referring now to FIG. 1, there is schematically illustrated the skull of an individual showing the individual's maxilla 12, mandible 14, upper and lower teeth 16 and 18, respectively, along the maxilla and mandible, and the tempromandibular joint, generally designated 20. The joint 20 comprises the condyle 22, the fossa 24 and a meniscus or cartilage 26 between the condyle 22 and fossa 24. The joint 20 typically forms the pivot point for the mandible. The musculature, not shown, for pivoting the mandible about the joint 20 includes the masseter, temporalis, sternocleidomastoid and trapezius muscles. As noted previously, during clenching, these muscles are flexed to bring pressure on the joint 20, tending to compress the joint, i.e., tending to displace the condyle toward the fossa with resultant swelling of the cartilage and bursa surrounding the joint, causing the symptoms and adverse effects of TMJS.

In accordance with the present invention, an appliance 28 is provided for relieving the pressure on the joint, thereby avoiding and relieving the adverse effects of TMJS. The appliance 28 is formed of a relatively soft thermoplastic dental material such as manufactured and sold by T&S Dental & Plastics Co., Inc. in sheet form of various thicknesses, preferably 0.150 inches thick and may be applied either to the teeth of the mandible or to the teeth of the maxilla. While the appliance is illustrated in the drawing figures as having a U-shaped arched configuration, it will be appreciated from the ensuing description that the contact points or fulcrums of the appliance 28 may be formed of separate discrete sections and applied bilaterally, respectively, to either the mandible or maxilla, without overlying the teeth between the fulcrums or contact points. In FIG. 1, the appliance 28 is generally U-shaped in cross-section, fitting along the top and opposite sides of the teeth of the mandible.

Figure 2:
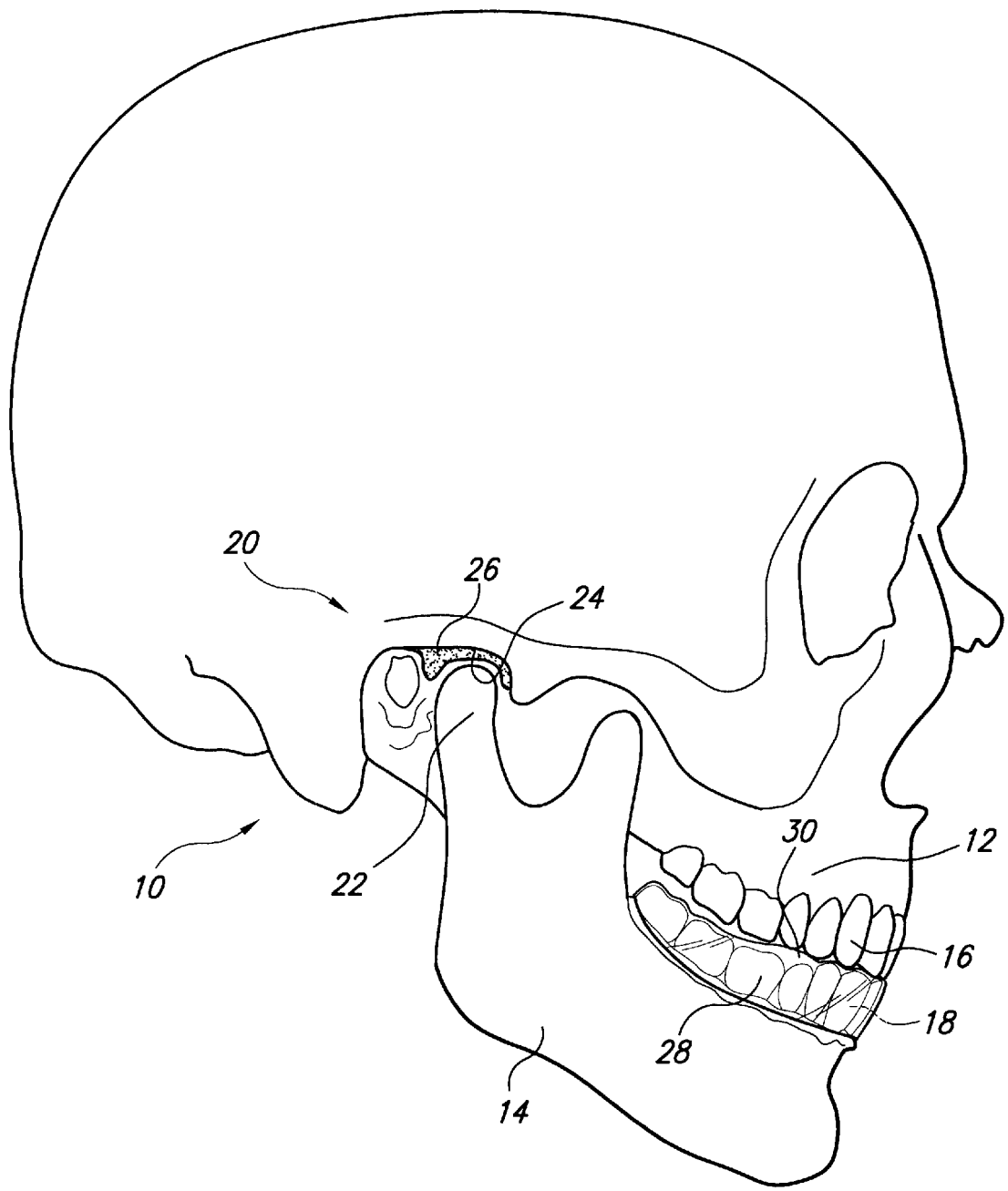
FIG. 2 is a view similar to FIG. 1 illustrating the appliance in use when the individual clenches his teeth.

In accordance with the present invention, the appliance 28 is formed with a fulcrum or contact point 30 on each of its opposite sides and generally in the area of the premolars. As illustrated in FIG. 1, with the contact points 30 in that area, the teeth anteriorly and posteriorly of the contact points do not contact one another or make contact with the appliance per se. Thus, as illustrated in FIG. 1, there are gaps between the appliance and the front and rear teeth of the maxilla on opposite sides of the contact points 30, the front gap being designated a. With that configuration, clenching of the teeth as illustrated in FIG. 2, with the contact points properly located, inherently results in the front teeth being is placed toward one another, closing the gap a and opening the gap long the teeth posteriorly. As illustrated in FIG. 2, the closing of the gap a between the front teeth by pivoting the mandible about the contact points 30 results in a relieving of the pressure on the joint 20. Particularly, as illustrated in FIG. 2, the condyle 22 tends to be displaced from the fossa 24, reducing the pressure on the bursa and also extending the musculature involved in clenching. Without the repeated compression on the meniscus caused by clenching, the meniscus is thereby allowed to heal. The pressure on the bursa is also reduced and the reduction in muscle strain eliminates spasms and headaches. As indicated previously, the appliance may be worn periodically by the individual, preferably during the night, when the clenching action typically occurs unconsciously.

Figure 3:
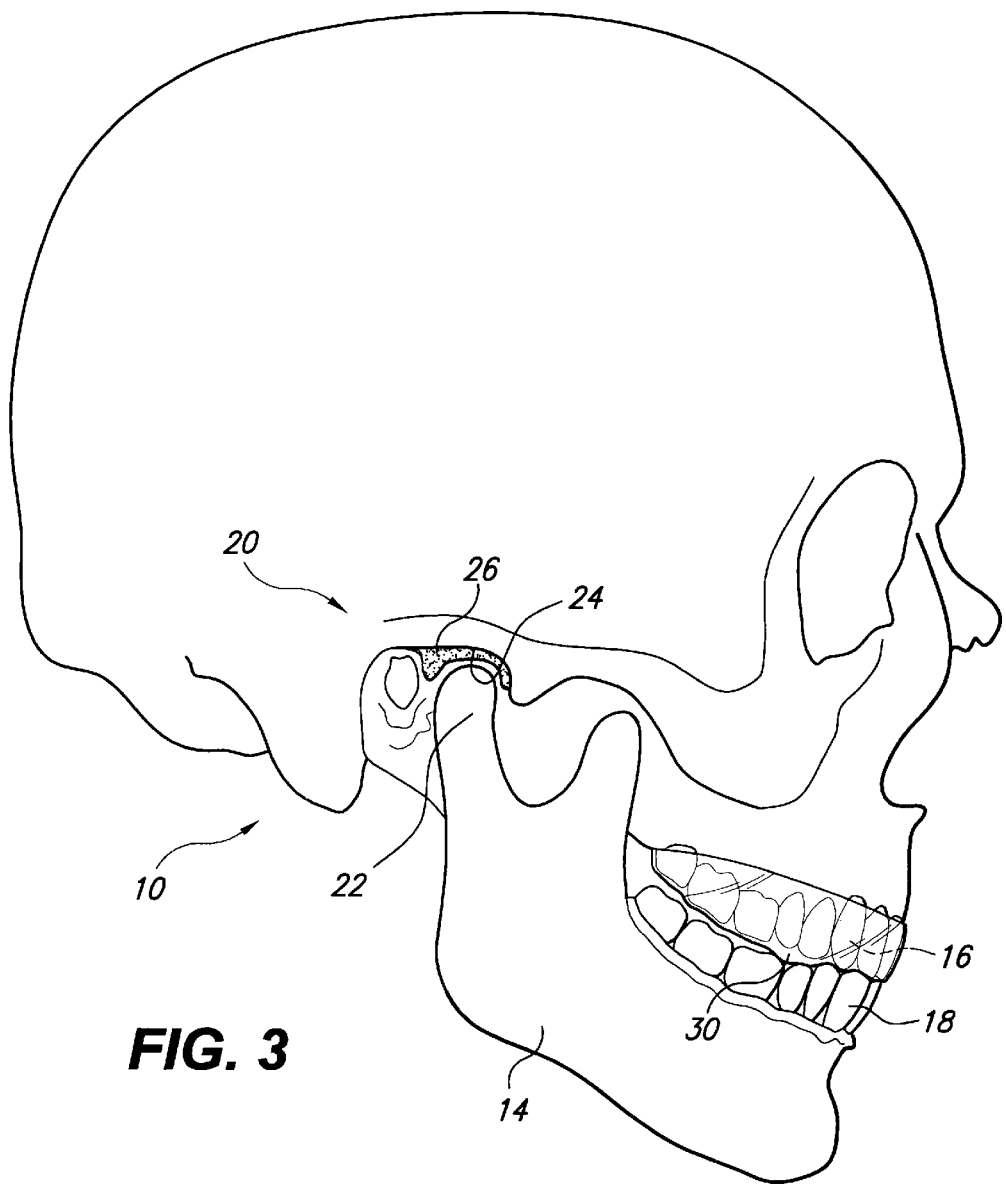
FIG. 3 is a view similar to FIG. 1 illustrating the appliance applied to the maxilla with the teeth being clenched.

Referring to FIG. 3, the appliance is shown illustrated along the teeth of the maxilla, with the contact points 30 bilaterally bearing on the teeth, preferably bisecting the premolars to a vertical midpoint of each. The same action, i.e., stress relief at the joint, occurs when the appliance is applied to the maxilla as when the appliance is applied to the mandible.

Figure 5:
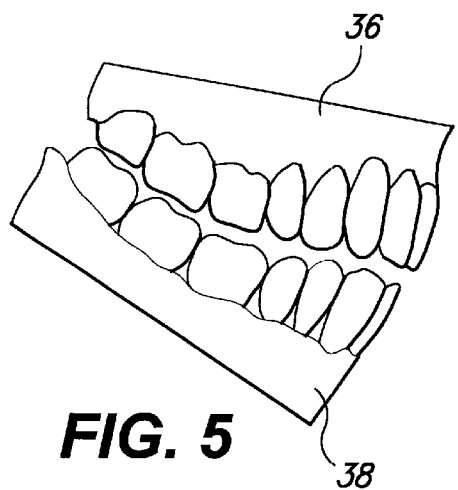
FIGS. 5–8 are schematic illustrations of a method of forming an appliance according to the present invention.

Referring now to FIGS. 5–8, there is illustrated a method of forming the appliance 28. In FIG. 5, there are illustrated positives 36 and 38 of impressions taken of the teeth of the maxilla and mandible of a TMJS-afflicted individual, i.e., the impressions being the negatives taken using standard dental procedures. The positives thus replicate the individual's teeth and their arrangement. It will be appreciated that the appliance in this representation is being formed to be worn on the teeth of the mandible. Thus, in FIG. 6, a notch 40 is formed at like bilateral locations along the positive of the teeth of the maxilla and at locations bisecting both premolars. The notches 40 may be formed by cutting or otherwise removing portions of the positive of the maxilla at that predetermined location. If the appliance is to be worn on the maxilla, the positive for the teeth of the mandible would have the notch cut bilaterally at the same predetermined location.

Figure 4:
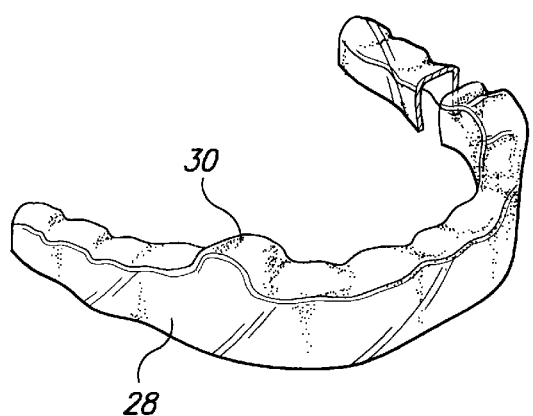
FIG. 4 is a perspective view of an appliance constructed in accordance with an embodiment of the present invention.
Figure 7:
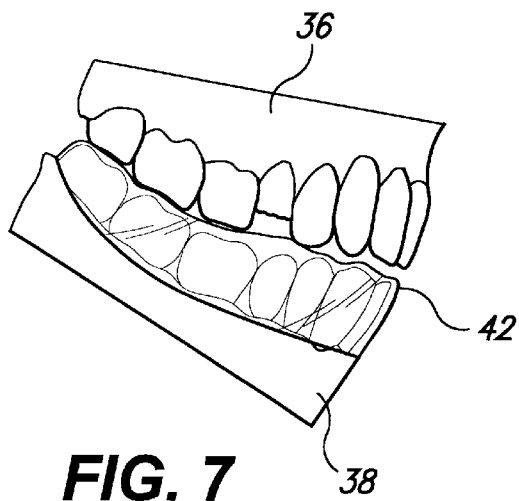
Figure 6:
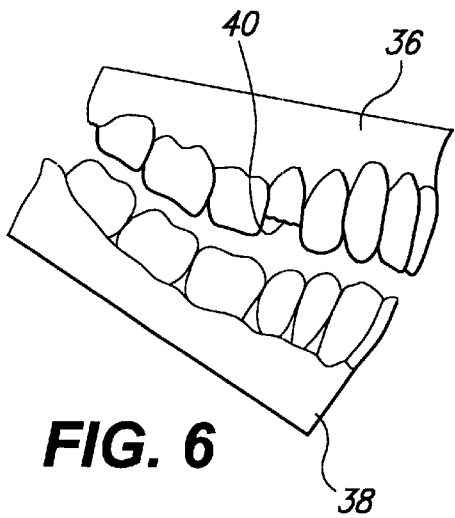
Figure 8:
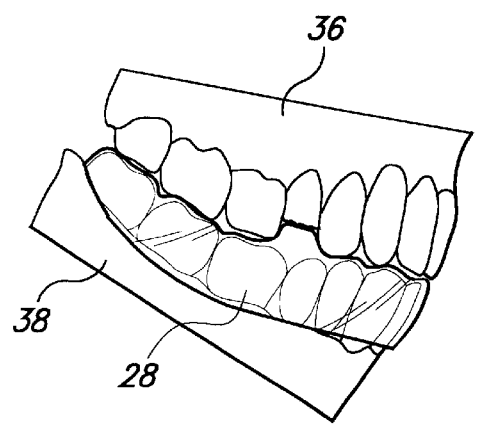

Referring to FIG. 7, the thermoplastic material 42 of the appliance is disposed about the teeth of the mandible in a vacuum former which is conventional dental equipment. As illustrated in FIG. 8, and while the thermoplastic material forming the appliance remains soft and formable, the positive 36 of the teeth of the maxilla is pressed into the thermoplastic material whereby portions of the material flow into the notches 40 in the positive of the maxilla. After cooling, the appliance 28 is removed from the positive of the mandible and appears similarly as illustrated in FIG. 4 with the contact points or fulcrums 30 raised from the surface of the appliance body above the remaining upper surfaces of the appliance 28 both anteriorly and posteriorly of the contact points 30. Because the notches 40 do not appear in the individual's actual teeth, i.e., in the teeth of the maxilla at the location of the premolars as illustrated, the appliance worn on the teeth of the mandible creates a pivot point for the mandible spaced from the normal pivot point between the condyle and fossa.

Figure 9:
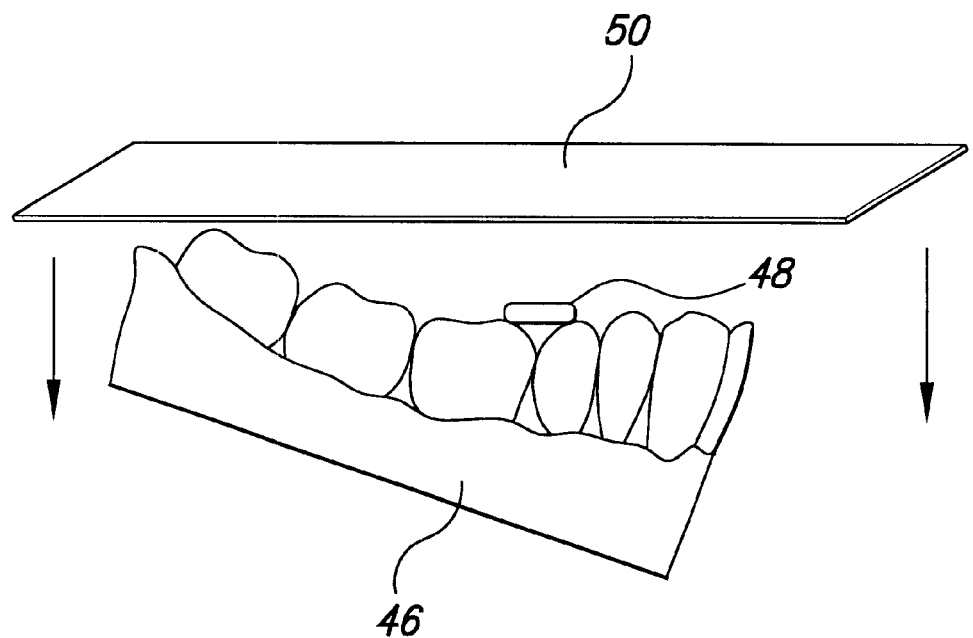
FIG. 9 is a schematic illustration of a further method of forming an appliance according to the present invention.

Referring now to FIG. 9, there is illustrated a further method of forming the appliance hereof. As illustrated in FIG. 9, a positive 46 of the mandible is illustrated. At each of the locations of the desired fulcrums on opposite sides of the positive 46, there is provided a plastic insert 48 formed of dental material. The insert 48 is thus located preferably at a location approximately over the second premolar and a portion of the first premolar of the positive 46, as illustrated. The insert may be placed on or adhered to the positive 46 at each location. The positive 46 with the insert 48 may then be disposed in a vacuum former and a sheet 50 of dental material is vacuum-formed, i.e., drawn about, the positive 46. It will be appreciated that the sheet 50 will thus form a pair of fulcrums at each of the locations of the inserts 48 whereby an appliance similar to the appliance illustrated in FIG. 4 is provided. It will be appreciated that this method of formation can be applied to the maxilla in a similar manner as described with respect to the mandible.

When an appliance formed by either of the above-described methods is worn by an individual, and the individual's teeth are clenched, the teeth tend to rotate about the bilateral contact points or fulcrums 30, closing the gap a between the front teeth and the appliance. This tends to displace the condyle away from the fossa. This action relieves the compressive pressure on the joint and extends the musculature rather than flexing the musculature as would otherwise be the case upon clenching of the teeth. As a consequence, and by wearing the appliance 28 only periodically, e.g., at night, the symptoms and adverse effects of TMJS are minimized or eliminated and over a short treatment period, e.g., a week's time. Moreover, should the effects of TMJS reappear subsequent to the treatment, the appliance may again be worn by the individual to alleviate it effects. Similarly, the treatment is non-invasive, requires only the formation of a dental appliance in a unique manner and in a novel configuration, is inexpensive, and may be repeated as many times as the symptoms of TMJS appear. Moreover, the treatment is most unobtrusive, i.e., the appliance need only be worn at night during sleep to obtain relief from TMJS.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An appliance for correcting tempromandibular joint syndrome comprising:
  a generally U-shaped appliance body for disposition along at least a portion of and along opposite sides of an arch of teeth on one of the mandible and the maxilla and having bilateral contacts projecting toward and for contacting another of the mandible and the maxilla, each of said contacts being located on said body adjacent the location of premolars of the arch of teeth and projecting beyond any other surface of said appliance body anteriorly and posteriorly of the contacts in a direction toward said another of the mandible and the maxilla, said contacts being located equidistantly along opposite sides of the body from an anterior midpoint of said one of the mandible and maxilla and serving as substantially non-compliant fulcrums enabling the mandible to pivot relative to the maxilla to relieve pressure on the tempromandibular joints and to extend musculature associated with the tempromandibular joints in response to clenching of the teeth.

2. An appliance according to claim 1 wherein the appliance body is formed of a soft thermoplastic material.

3. An appliance according to claim 1 wherein said appliance body is for disposition along the teeth of the mandible, said contacts being located along said appliance body at approximately the locations of the second premolars of the mandible.

4. An appliance according to claim 1 wherein said appliance body is for disposition along the teeth of the mandible, said contact being located along said appliance body at locations substantially bisecting the premolars.

5. An appliance according to claim 1 wherein each of said contacts has a depth of projection from said body sufficient to provide a gap between an individual's teeth anteriorly and posteriorly of said contacts upon closure of the contacts with the teeth of said another of the mandible and the maxilla.

6. A method of treating tempromandibular joint syndrome comprising the steps of:

relieving the pressure on the tempromandibular joint by (i) applying an appliance along the teeth of one of the mandible and maxilla and (ii) pivoting the mandible relative to the maxilla about raised bilateral contact points along the appliance projecting toward and contacting the teeth of another of the mandible and maxilla in a direction tending to displace the condyle away from the fossa.

7. A method according to claim 6 including applying the appliance having bilateral sections with raised contact points along the teeth of one of the mandible and maxilla at locations wherein the contact point of each section overlies portions of at least one premolar.

8. A method of forming an appliance for correcting tempromandibular joint syndrome comprising the steps of:

forming an impression of the teeth of an individual's mandible and maxilla;

forming a positive of the teeth of the mandible and maxilla from the impressions;

providing bilateral notches in the teeth of one of the positives of the teeth of the mandible and maxilla;

forming a soft plastic material about the teeth of another of the positives of the mandible and maxilla to form an appliance body; and while the thermoplastic material is soft and formable, relatively closing the positives of the teeth of the mandible and maxilla toward one another such that the plastic material enters the notches, thereby forming an appliance having raised bilateral contact points for projecting toward opposed registering teeth in use.

9. A method of forming an appliance for correcting tempromandibular joint syndrome comprising the steps of:

forming an impression of the teeth of an individual's mandible or maxilla;

forming a positive of the teeth of the mandible or maxilla from the impression;

providing inserts at predetermined bilateral locations along the positive of the teeth of the mandible or maxilla; and forming a soft plastic material about the inserts and the positive of the teeth of the mandible or maxilla to form an appliance body having raised bilateral contact points for projecting toward opposed registering teeth when the appliance is worn by an individual.

10. A method according to claim 9 including applying the inserts along the positive of the mandible or maxilla at locations where the inserts contact portions of at least one premolar on each of the opposite sides of the positive of the teeth of the mandible or maxilla.

* * * * *